United States Patent
Lee et al.

(10) Patent No.: US 11,382,789 B2
(45) Date of Patent: Jul. 12, 2022

(54) THERMAL THERAPY SYSTEM AND METHOD OF USE

(71) Applicant: RHMD PTY. LTD., Croydon (AU)

(72) Inventors: Martin Lee, Croydon (AU); Craig Kelley, Wilson, WY (US); Robert Biolchinni, Jackson, WY (US); Steven Stokes, Jackson, WY (US)

(73) Assignee: RHMD PTY. LTD., Croydon (AU)

( * ) Notice: Subject to any disclaimer, the term of this patent is extended or adjusted under 35 U.S.C. 154(b) by 27 days.

(21) Appl. No.: 16/230,143

(22) Filed: Dec. 21, 2018

(65) Prior Publication Data
US 2019/0117445 A1 Apr. 25, 2019

Related U.S. Application Data (63) Continuation of application No. 13/837,958, filed on Mar. 15, 2013, now abandoned.
(Continued)

(51) Int. Cl.
*A61F 7/02* (2006.01)
*A61F 7/00* (2006.01)

(52) U.S. Cl.
CPC ...... *A61F 7/007* (2013.01); *A61F 2007/0029* (2013.01); *A61F 2007/0039* (2013.01);
(Continued)

(58) Field of Classification Search
CPC .............. A61F 7/007; A61F 2007/0091; A61F 2007/0029; A61F 2007/0039;
(Continued)

(56) References Cited

U.S. PATENT DOCUMENTS

| 4,860,748 A | * | 8/1989 | Chiurco | .................. | A61F 7/007 |
| | | | | | 607/96 |
| 5,603,728 A | * | 2/1997 | Pachys | ..................... | A61F 7/02 |
| | | | | | 607/104 |

(Continued)

FOREIGN PATENT DOCUMENTS

| CA | 2214269 A1 | 9/1996 |
| GB | 2077595 A | 12/1981 |

(Continued)

OTHER PUBLICATIONS

International Search Report and Written Opinion, issued by I.S.A./U.S. in regard to corresponding international patent application Serial No. PCT/US2013/045182, dated Nov. 14, 2013, 8 pages. USA.

(Continued)

*Primary Examiner* — Joanne M Hoffman
*Assistant Examiner* — Yasamin Ekrami
(74) *Attorney, Agent, or Firm* — Dentons US LLP (57) ABSTRACT

A system that can be used to provide highly controlled thermal therapy and compression to both cool and heat a skin surface and a joint and surrounding tissue below the skin surface is provided. The system includes a joint conforming wrap; a power supply module for supply power to the joint conforming wrap and a cable operably coupling the wrap and the power supply module. The joint conforming wrap and power supply module include opposing thermoelectric modules. The joint conforming wrap is designed to provide heat transfer processes to the body of a patient to warm or cool the skin and a joint and surrounding tissue disposed under the skin.

17 Claims, 6 Drawing Sheets

Related U.S. Application Data (60) Provisional application No. 61/658,028, filed on Jun. 11, 2012.

(52) U.S. Cl.
CPC .............. *A61F 2007/0054* (2013.01); *A61F 2007/0075* (2013.01); *A61F 2007/0091* (2013.01); *A61F 2007/0096* (2013.01)

(58) Field of Classification Search
CPC ...... A61F 2007/0054; A61F 2007/0075; A61F 2007/0096
See application file for complete search history.

(56) References Cited

U.S. PATENT DOCUMENTS

| | | | | |
|---|---|---|---|---|
| 5,653,741 A | * | 8/1997 | Grant | A61F 7/007 607/114 |
| 6,840,955 B2 | | 1/2005 | Ein | |
| 2003/0125649 A1 | | 7/2003 | McIntosh et al. | |
| 2007/0255362 A1 | | 11/2007 | Levinson et al. | |
| 2008/0058911 A1 | * | 3/2008 | Parish | A61F 7/0085 607/104 |
| 2008/0077211 A1 | * | 3/2008 | Levinson | A61F 7/10 607/108 |
| 2008/0132816 A1 | | 6/2008 | Kane et al. | |
| 2008/0132976 A1 | | 6/2008 | Kane et al. | |
| 2008/0188915 A1 | * | 8/2008 | Mills | A61F 7/007 607/112 |
| 2010/0217361 A1 | | 8/2010 | Kulstad et al. | |

FOREIGN PATENT DOCUMENTS

| | | |
|---|---|---|
| GB | 2422109 A | 7/2006 |
| WO | WO-2007120639 A2 | 10/2007 |

OTHER PUBLICATIONS

Extended European Search Report and Opinion, issued by the European Patent Office, regarding corresponding patent application Serial No. EP 13804137.1, dated Feb. 17, 2016, 7 pages. EPO.

\* cited by examiner

THERMAL THERAPY SYSTEM AND METHOD OF USE

RELATED APPLICATION DATA

This application is a continuation of U.S. patent application Ser. No. 13/837,958, filed on Mar. 15, 2013; which claims the benefit of provisional application U.S. Ser. No. 61/658,028, filed on Jun. 11, 2012; the entireties of which are incorporated herein by reference.

FIELD OF THE INVENTION

The present invention relates to the cooling and/or heating of a skin surface and a joint and surrounding tissue below the skin surface to alleviate pain. More specifically, the present invention relates to an apparatus that can be used to provide highly controlled thermal therapy and compression to both cool and heat a skin surface and a joint and surrounding tissue below the skin surface.

BACKGROUND OF THE INVENTION

Injury to joints and the surrounding tissue may result from a variety of activities such as for example surgery and sports injuries. Acute injuries to joints are sudden, sharp, traumatic injuries that occur immediately (or within hours) and cause pain (possibly severe pain). Most often acute injuries result from some sort of impact or trauma such as a fall, sprain, or collision. Acute injuries also cause common signs and symptoms of injury such as pain, tenderness, redness, skin that is warm to the touch, swelling and inflammation.

Chronic injuries to joints, on the other hand, can be subtle and slow to develop. They often cause dull pain or soreness and are often the result of overuse. Cold therapy with ice is the best immediate treatment for acute injuries because it reduces swelling and pain. Thus, in cases in which an acutely injured joint is to be treated, compression and cold are applied to control the swelling and the commonly occurring hemarthrosis that causes pain and delays rehabilitation. Modalities for postoperative cold and compression traditionally have been applied separately—the compression most commonly by an elastic bandage wrapped around the injured body part, and the cold by a superimposed plastic bag filled with ice. While this approach is simple and can be economical, it has its own complications including minimal re-usability of the elastic bandage, short life span until the ice melts and non-uniform application of cold and compression due to gradual warming of the fluid in the vicinity of the patient and irregular distribution of ice in the bag. Further, these systems are subject to leakage and can only supply a cooling effect for a limited period of time. There is also controversy as to whether continued application of ice results in a sudden vasodilation of the blood vessels (the hunting response) and if so, at what time this response begins and how often a cycle of constriction and dilation occurs.

Heat, on the other hand, is generally used for chronic injuries or injuries that have no inflammation or swelling. Sore, stiff, nagging muscle or joint pain is ideal for the use of heat therapy. Athletes with chronic pain or injuries may use heat therapy before exercise to increase the elasticity of joint connective tissues and to stimulate blood flow. Heat can also help relax tight muscles or muscle spasms.

To address some of the foregoing problems, certain devices have been developed that apply compression and cold therapy in a unitary compression system. Although these systems work well for applying compression and cold therapy to the injured body part, there is no unitary system that is capable of providing both cold and heat therapy. In addition, issues remain with devices for applying cold to injured joints including the non-uniform application of the cold, leakage, and cumbersome cooling systems attached to a compression bandage affecting patient mobility.

Therefore, alternatives to these systems are needed, which provide compression and well controlled uniform cooling and heating in a leak free system and which are simpler to use and less cumbersome to patient mobility.

BRIEF SUMMARY OF THE INVENTION

The shortcomings of conventional systems are addressed by the thermal therapy system in accordance with the invention.

In one aspect of an exemplary thermal therapy system, the system includes a joint conforming wrap, a power supply module and a cable in operable communication with the wrap and the power supply module.

In another aspect of an exemplary thermal therapy system, the thermal therapy may include delivering energy of any wavelength from the electromagnetic spectrum, including radiofrequency, microwave, ultrasound, high intensity focused ultrasound, low intensity focused ultrasound, infrared waves, electrical energy, laser energy, other sources of thermal energy, and combinations of the foregoing. The thermal therapy may also comprise cooling.

In another aspect of an exemplary thermal therapy system, the joint conforming wrap includes a first chamber for housing an inflatable member such as a bladder and a second chamber for housing one or more N-P Stack/thermoelectric modules therewithin. The thermoelectric modules may be made from alternating p-type and n-type semiconductor elements connected by metallic connectors. Charge flows through the n-type element, crosses a metallic interconnect, and passes into the p-type element. If a power source is provided, the thermoelectric module may act as a cooler/heater, this known as the Peltier effect but may also employ other effects such as the Seebeck & Thomson effects. Electrons in the n-type element move opposite the direction of current and holes in the p-type element will move in the direction of current, both may be removing heat from one side of the device. This may be called a NP Stack. When a heat source is externally provided, the thermoelectric device may function as a power generator. The heat source drives electrons in the n-type element toward the cooler region, creating a current through the circuit. Holes in the p-type element then flow in the direction of the current. N-P Stack/Thermoelectric modules will be referred to herein as thermoelectric modules.

In one aspect of the invention the bladder is in fluid communication with a fluid compression pump; the fluid compression may be delivering air or a liquid to the bladder. The second chamber housing the one or more thermoelectric modules is in fluid communication with the heat exchanger. The thermoelectric modules have a Peltier or Seebeck effect. The outside of the second chamber containing the one or more thermoelectric modules therewithin is designed to provide heat transfer processes to the body of a patient to warm or cool the skin and a joint and surrounding tissue disposed under the skin.

In another aspect of the invention the power supply module includes a heat exchanger unit in communication with the thermoelectric modules in the joint conforming wrap, a fluid compression pump and a controller. The heat exchanger unit includes a thermoelectric module for heating and cooling, which transfers heat into or out of a thermal liquid disposed in the heat exchanger, and a fluid circulation pump. The heat exchanger unit, electrical power supply and fluid compression pump are operably coupled to and controlled by the controller. The controller controls the operation of the heat exchanger unit to control the thermal characteristics, for example heating or cooling, of the thermal liquid disposed in the heat exchanger. The controller/microprocessor also controls the electrical power supply for supplying power to the thermoelectric modules in the joint conforming wrap.

In a further aspect of the invention, the controller controls the operation of the fluid circulation pump, the fluid compression pump and the electrical power supply. The fluid circulation pump circulates thermal liquid in a closed or open loop system between the heat exchanger unit and the second chamber permitting heat transfer to or from the heat exchanger to the thermoelectric modules via the thermal fluid.

In a further aspect of the invention, the compression therapy system also includes a user interface that is in operable communication with a controller that permits a user to manually control the temperature of the system and the duration of treatment.

In a further aspect of the invention, the compression therapy system may comprise a closed loop or an open loop system.

In a further aspect of the invention, the compression therapy system may be removably coupled to a power supply unit or may be permanently coupled to a power supply unit.

In a further aspect of the invention an interactive keyboard display is provided for inputting data into the power supply module, such as duration of therapy and desired temperature.

In another aspect of the invention a microchip including software is contained within the power supply module for managing the relationship between the two opposing thermoelectric module configurations, i.e. the thermoelectric modules in the joint conforming wrap and the thermoelectric element in the power supply module.

In another aspect of the invention PC hard wire, global positioning system, cellular and internet capabilities are provided.

In another aspect of the invention, the cold compression therapy system may comprise a closed loop system in which the same thermal liquid is circulated throughout the system or an open loop system in which the thermal liquid may be changed out.

In another aspect the closed loop system may be removably coupled to or permanently attached to the power supply module.

In another aspect the open loop system is removably coupled to the power supply module.

In another aspect of the cold compression therapy system, the system may be cooled by a liquid, a solid, or a gas. The solid may include ice or chemical packs. The chemical packs may include an ionic compound such as ammonium chloride or ammonium nitrate that reacts with a non-ionic compound such as water. The cooling solid may be removably changed.

The system in accordance with the invention has the ability to measure and control temperature at the point of contact on the patient's skin. The system also has the ability to set, measure, and record duration (time) and temperature during use.

The dual thermoelectric module arrangement (in the joint conforming wrap and in the power supply module) may include a plurality of thermoelectric modules or may include a single thermoelectric module.

Air circulating through the system may be cooled from a floor unit where the air is forced or compressed through a channel to cool the hot side of the thermoelectric module arrangement and vented out an exhaust port.

The joint conforming wrap may be encased in a hard case or soft case that is removably coupled to or permanently attached to the power supply module. The joint conforming wrap may also in a hard or soft adjustable compression case that cycles with the thermoelectric modules in the joint conforming wrap.

While multiple embodiments, objects, features, and advantages are disclosed, still other embodiments of the invention will become apparent to those skilled in the art from the following detailed description taken together with the accompanying figures, the foregoing being illustrative and not restrictive.

BRIEF DESCRIPTION OF THE DRAWINGS

For a better understanding of the invention, and to show how the same may be carried into effect, reference will now be made, by way of example, to the accompanying drawings, in which.

DETAILED DESCRIPTION OF THE INVENTION

Figure 1:
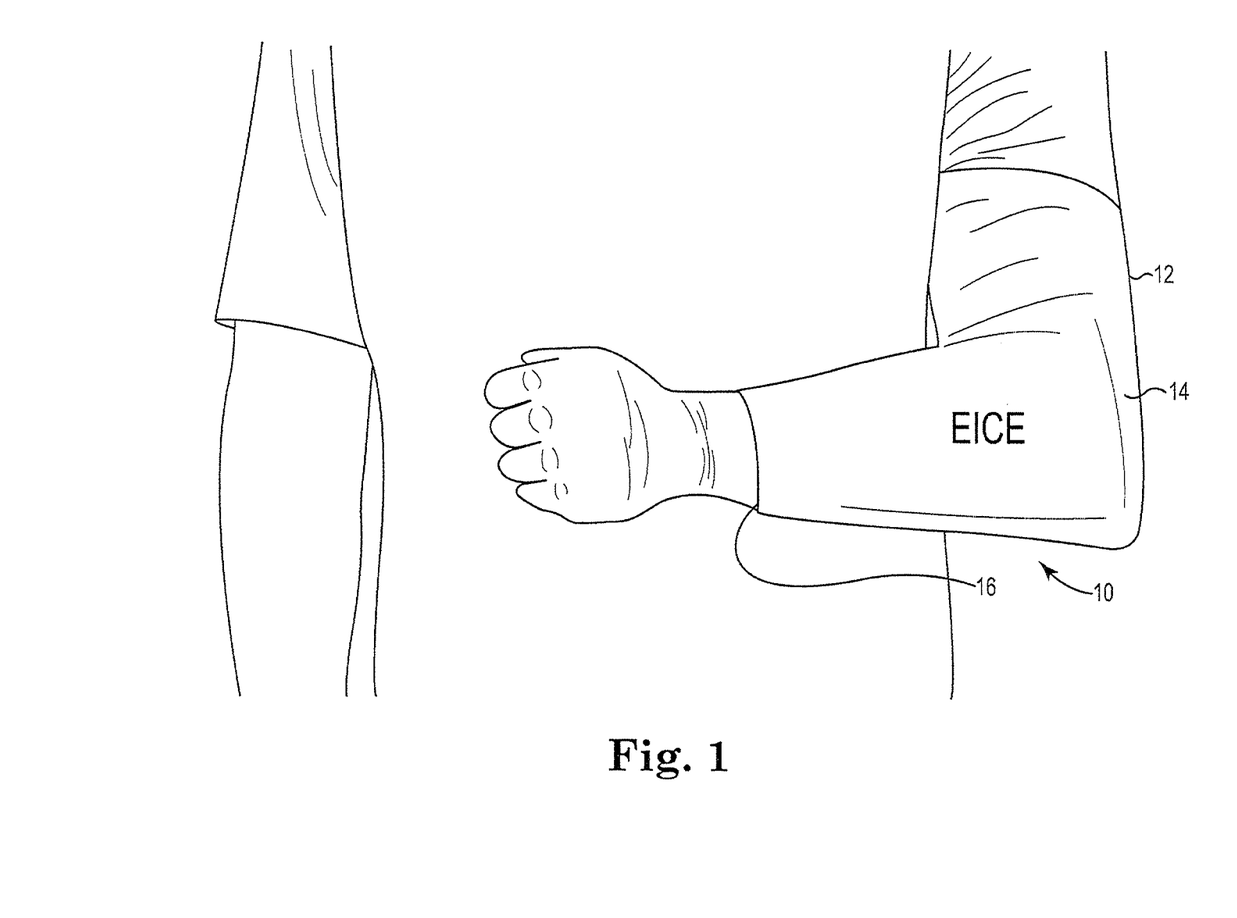
FIG. 1 is an illustration of an exemplary compression device for use on an elbow in accordance with the invention.

Referring now to FIG. 1, a joint conforming compression wrap 12 for use on an elbow is shown. Those of skill in the art will appreciate that an elbow wrap is shown by way of illustration and not of limitation and that wraps used for ankles, elbows, knees, and hip, for example, are within the intended scope of the invention. The shape, contour and construction of the wrap will depend on the specific joint covered. The wrap will circumferentially surround, either wholly or in part, the particular joint needing therapy and includes a first outer surface 14 and a second skin contacting surface 16. Those of skill in the art will appreciate that the wrap 12 may be entirely elastomeric, such as a woven elastic material, or may include a hard shell, such as a polycarbonate, with a soft lining.

Figure 2A:
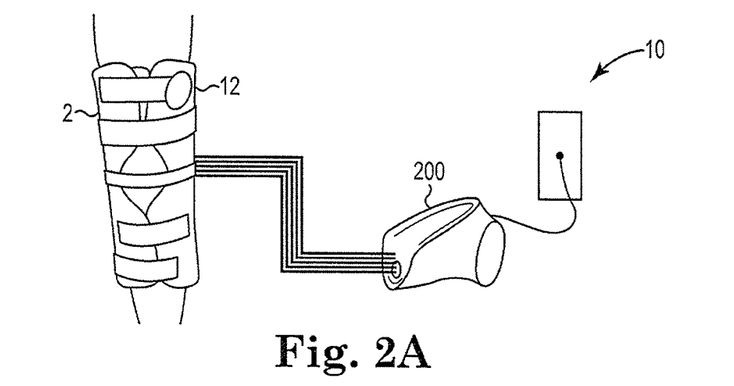
FIGS. 2A and 2B are illustrations of an exemplary compression system that is permanently attached to a power supply in accordance with the invention.
Figure 3A:
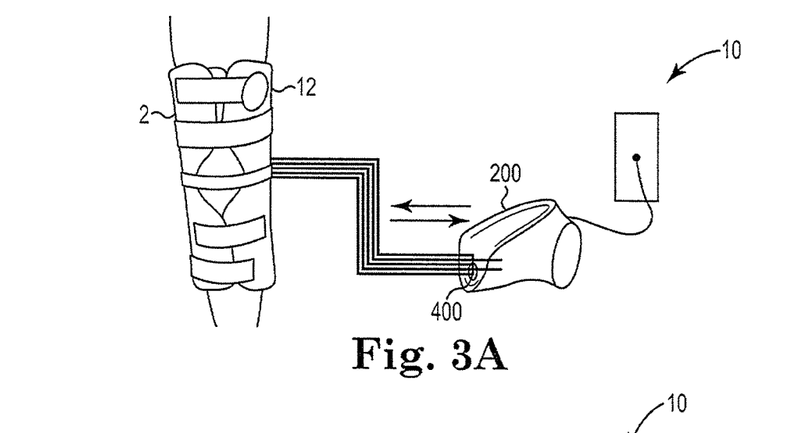
FIGS. 3A and 3B are illustrations of an exemplary compression system that is removably coupled to a power supply in accordance with the invention.

The joint conforming wrap may be encased in a hard case or soft case that is removably coupled to or permanently attached to the power supply module as best seen in FIGS. 2A and 3A. The joint conforming wrap may also in a hard or soft adjustable compression case that cycles with the thermoelectric modules in the joint conforming wrap.

Referring generally now to FIGS. 2-6 the compression therapy system in accordance with the invention will be described. The compression therapy system broadly includes a joint conforming wrap 12 to cover the joint of interest, a power supply module 200 and a cable operably coupling the wrap 12 and the power supply module 200.

Figure 5:
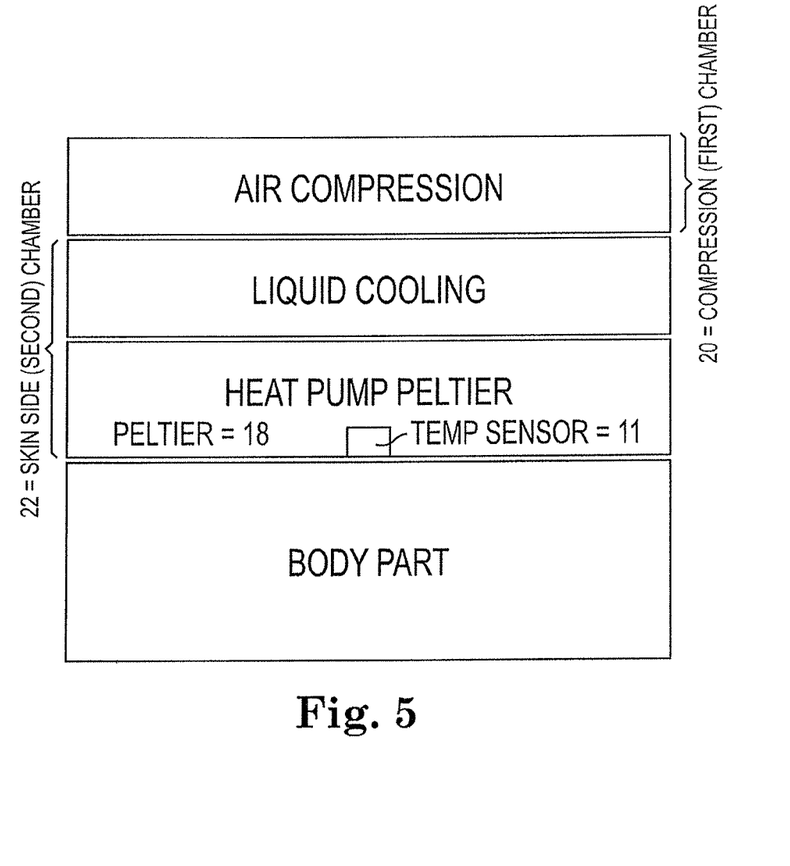
FIG. 5 is an illustration of a compression system in accordance with the invention.

Although the system operates as a unit, the joint conforming wrap will be discussed first. The joint conforming wrap 12 includes a hard or soft casing and may include a liner (not shown) that comes into contact with the patient's skin. The joint conforming wrap includes a first chamber 20 and a second chamber 22. The joint conforming wrap further includes a first outer surface 14 and a second skin contacting surface 16 designed to contact a patient's skin.

First chamber 20 includes an inflatable member 24, such as a bladder, disposed therewithin. Inflatable member 24 is designed to compress the second skin contacting side 16 of the wrap 12 into contact with the skin surface 28 when fluid compression pump 236 is activated by controller 238.

Second chamber 22 may be encased in a thermally conductive fabric comprising nylon, polyesters or combinations of the foregoing and a metal such as aluminum, copper, silver or other metals, or other materials known to those of skill in the art. The thermally conductive fabric may be in contact with the second skin contacting surface 16 of wrap 12. Alternatively, the thermally conductive fabric may comprise the skin contacting surface 16 of wrap 12. As will be discussed below, the second skin contacting surface 16 of the wrap 12 in contact with the patient's skin may be warm or cold depending on the desired therapy.

Second chamber 22 includes one or more thermoelectric modules 18 therewithin. Those of skill in the art will appreciate that while four thermoelectric modules 18 are depicted there may be a single thermoelectric module or multiple thermoelectric modules utilized. The thermoelectric modules 18 are operably coupled to controller 238, electrical power supply 234 and fluid circulation pump 232 via conduits 310, 312, 314, 316.

One or more temperature sensors 11 are positioned in second chamber 22 close to the skin. Temperature sensors 11 sense the temperature of the skin and provide feedback to controller 238 to regulate the temperature of the thermal fluid in contact with the thermoelectric modules.

Figure 4:
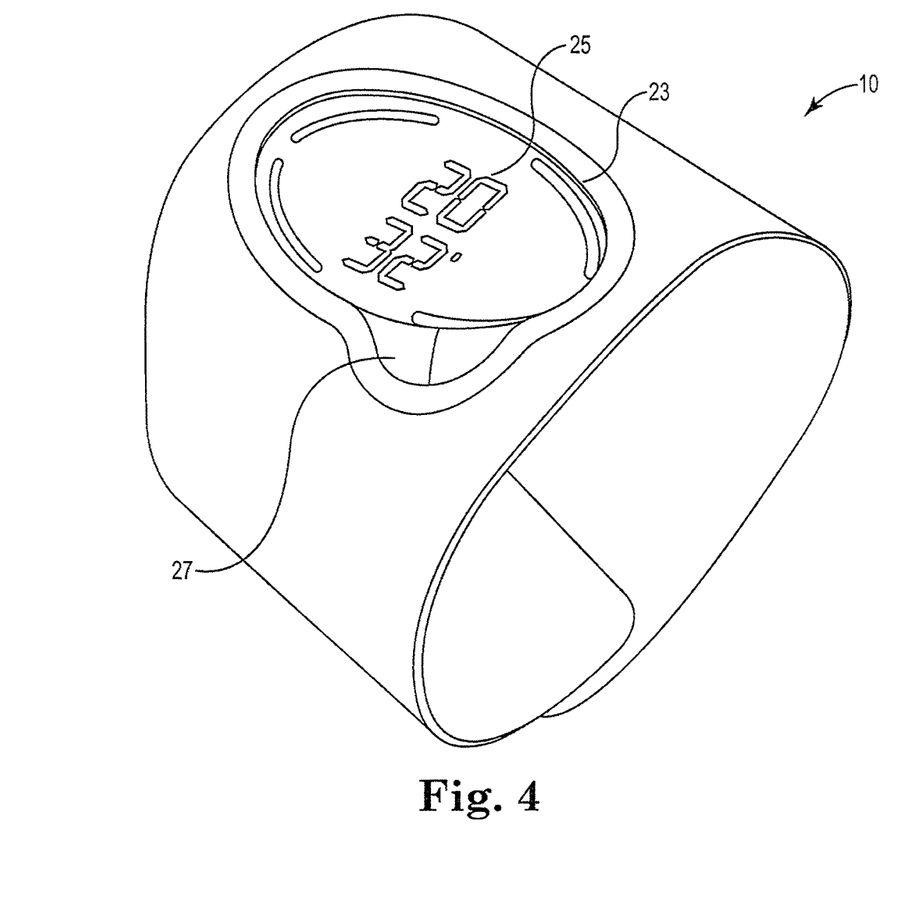
FIG. 4 is an exemplary compression system showing a time and temperature control on the exterior of the compression system.

Joint conforming wrap 12 may also include a digital display 23 on an outer surface 14 thereof. Digital display and control options 23 are operably coupled to electrical power supply and thermoelectric modules 18 and controller 238. As best seen in FIG. 4 digital display and control options 23 include digital display 25 for displaying temperature and duration of therapy in minutes. Control options 27 include user controlled input buttons to control temperature and duration of therapy.

Figure 2B:
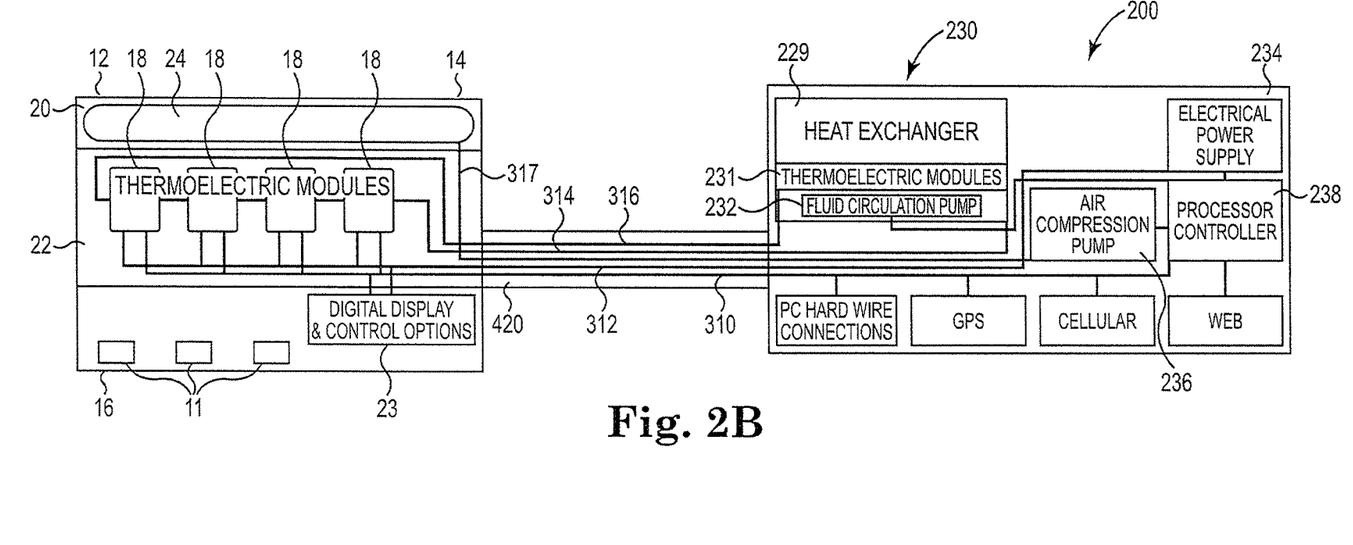
Figure 3B:
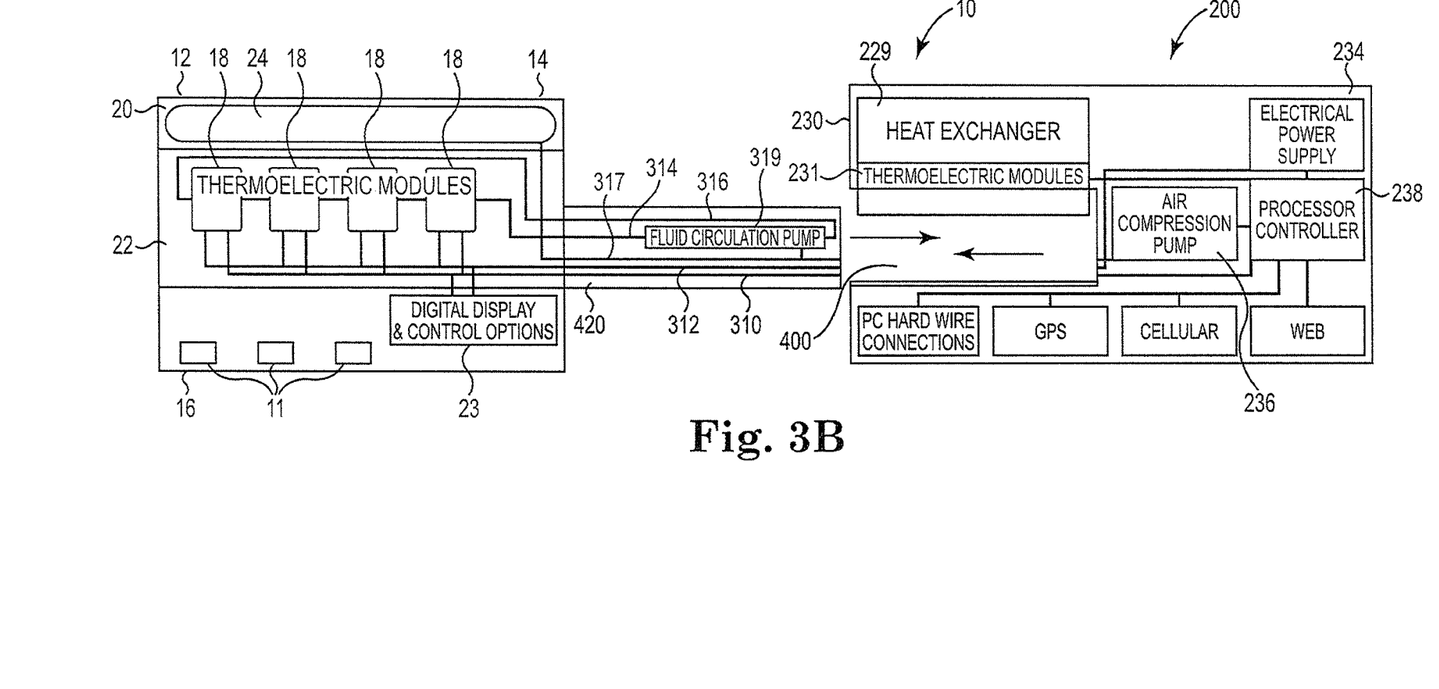

Referring now to FIGS. 2B and 3B, the power supply module will now be discussed. The power supply module 200 broadly includes a heat exchanger unit 230, an electrical power supply 234, a fluid compression pump 236 and controller 238.

Heat exchanger unit 230 includes heat exchanger 229, thermoelectric modules 231 and fluid circulation pump 232. Thermoelectric modules 231 may comprise one thermoelectric module or multiple thermoelectric modules and correspond in number to the thermoelectric modules 18 in joint conforming wrap 12. Fluid circulation pump 232 is operably controlled by controller 238 to pump a thermal fluid (not shown) through the thermoelectric modules 231 and heat exchanger 229. Fluid circulation pump 232 also controls fluid flow between the heat exchanger unit 230 and the one or more thermoelectric modules 18 in wrap 12. The heat exchanger unit 230 also includes one or more fans to evacuate heat from the heat exchanger and from the power supply module. The heat exchanger 230 is in fluid communication with the second chamber 22 via a first thermal fluid circulation conduit 310 and a second thermal fluid circulation conduit 312 in cable 316. In its simplest form, the thermal fluid may comprise water. Thermal fluid may also comprise a mixture of water, ethylene glycol, propylene glycol and other thermal fluids known to those of skill in the art.

The system in accordance with the invention provides a high level of thermal control via the one or more thermoelectric modules 231. The thermoelectric modules 231 comprise micro heat pumps that are capable of rapid pump rates. The heat generated by the thermoelectric modules may be managed by heat exchanger 229 in the following manner. Thermal fluid is pumped by fluid distribution pump 232 to contact the surface of the thermoelectric modules 231 in an exemplary continuous closed loop system. The thermal fluid may be cooled by the heat exchanger 229. The heat exchanger 229 may not always need to be operating. Rather this is controlled by controller 238 based on temperature input data selected by a user, sensors 11 and associated algorithms. The sensors 11 provide an empirical measure of the subject heat transfer relationships. Those of skill in the art will also appreciate that custom thermoelectric modules 231 may also be used and may include integral (built-in) thermal management.

Fluid compression pump 236 provides a source of air fluidly coupled to the inflatable member 20 within wrap 12 for inflating and deflating the inflatable member 12 to control the compression of the second patient skin contacting side 16 of wrap 12 against the patient's skin.

Electrical power supply 234 is operably coupled to the controller 238 in the power supply module 200 and the one or more thermoelectric modules 18 within second chamber of wrap 12. Electrical power supply 234 provides the various energy levels, which may be voltages, needed by the controller 238. Electrical power supply is not limited to electric means but may also comprise batteries.

The controller 238 includes a user interface (not shown) that allows a user to manually control the temperature of the system, the duration of treatment and other aspects of the system. The user interface may also include a touch screen or may be capable of remote cellular operation from a "smart phone"; by a personal computer via hard wire connection; and/or via the Internet.

Cable 316 may be permanently or removably coupled to the power supply module 200. If cable is removably coupled to the power supply module 200 then power supply module may include coupling channel 400, as best seen in FIG. 3B. The coupling channel 400 may be in operable communication with the thermoelectric module 231 and operably connect with the electrical power supply 234 and the fluid compression pump 236. If cable 316 is removably coupled to the power supply supply module 200 then fluid circulation pump 319 is positioned within the cable 316 and moves fluid through the system. In this case, fluid circulation pump 232 is not needed in power supply module 200.

Cable 316 comprises a thermal conductive material on an outer surface thereof and contains a lumen 420 therewithin. Lumen 420 operably receives fluid flow conduits 314, 316, fluid compression conduit 317, electrical power conduit 312 and digital conduit 310. Fluid flow conduit 314 supplies thermal fluid from the heat exchanger unit 230 pumped by fluid distribution pump 232. Fluid flow conduit 316 returns thermal fluid from the thermoelectric modules 18 to the heat exchanger 230. Fluid compression conduit 317 supplies air to inflatable member 24 from fluid compression pump 236. Electrical power conduit 312 supplies power from electrical power supply 234 to thermoelectric modules 18 and digital display and control options 23. Digital conduit 310 operably couples controller 238 (and PC, GPS, cellular and Internet capabilities) with thermoelectric modules 18 and digital display and control options 23.

In operation, a user inputs a desired temperature and time duration into user interface, as best seen in FIG. 4. An activation button may be pressed, which activates the controller. The controller sends a signal to the fluid circulation pump 232 to activate. In a closed loop system the thermal liquid (not shown) is circulated by the fluid circulation pump 232 through the heat exchanger 230 and pumped through the first thermal fluid circulation conduit 310 and through the thermoelectric modules 18 to the second thermal fluid circulation conduit 312. As the thermal fluid flows through the thermoelectric modules it cools the thermoelectric modules. As the thermoelectric modules 18 are cooled, the thermally conductive fabric will transfer the cooling effect to the skin. As the thermal fluid flows to the second thermal fluid circulation conduit 312 heat is removed from the "hot side" of the thermoelectric modules and then it recirculates back to the heat exchanger 230 and the cycle repeats.

If a user desires a "heating" therapy effect to the joint, no physical manipulation of the joint conforming wrap 12 is needed. Rather, the user inputs the desired temperature and time duration into the user interface operably coupled to controller 238. The controller 238 sends a signal to thermoelectric modules 18 to reverse polarity thus turning the "cold" skin side to a "hot" skin side.

The thermal fluid may be a water/propylene glycol or propylene glycol, any relatively inert fluid having suitable heat capacity and viscosity characteristics. The thermal fluid may be selected, or may include an additive, to retard bacterial growth if the second chamber of wrap leaks.

As the thermoelectric modules 18 are cooled and/or heated, the thermally conductive fabric may transfer the cooling/heating effect to the skin and the adjacent joint providing cold and heat therapy to a patient.

Figure 6:
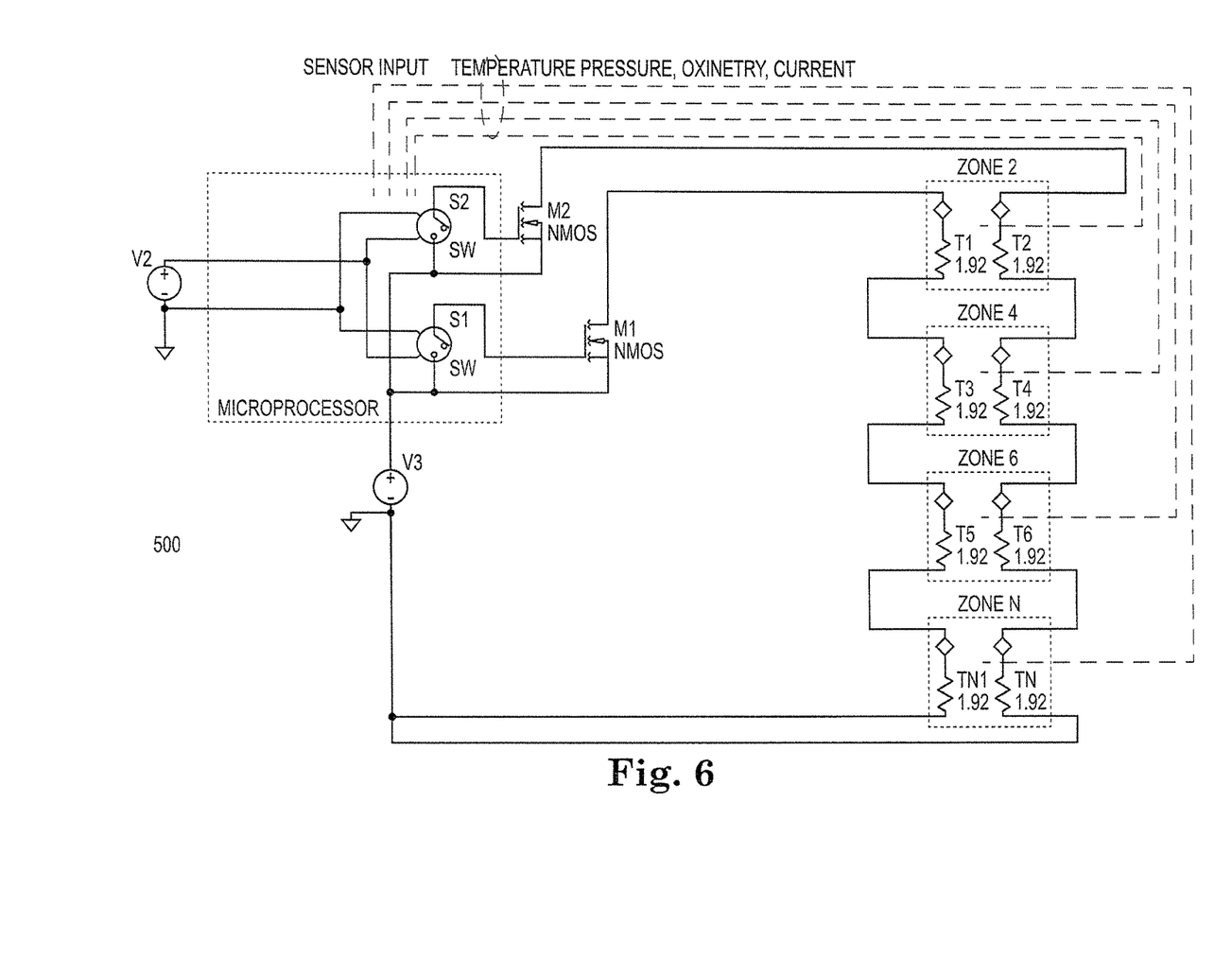
FIG. 6 is a schematic of an exemplary power supply unit in accordance with the invention.

Referring now to FIG. 6 a schematic of a power supply module in accordance with the invention where V # represents voltage sources required for powering processes requiring various power levels. S # represents digital switching functions within microprocessor, which offers various algorithm options for controlling the thermoelectric module zones. M # represents digital/high voltage switching. Switching may be provided by various technologies including solid-state and/or mechanical means. T # represents thermoelectric modules. Multiple thermoelectric modules may be assembled to produce a zone. Those of skill in the art will appreciate however that a single thermoelectric module may be used. Sensor input may be provided to microprocessor by various elements such as thermocouples. Power is distributed to the various zones based on sensor input into the controller.

This cold compression therapy system in accordance with the invention will be utilized in a business method as follows. The system will be rented to a user in units of time. An owner of the system will maintain ownership of and title to all the manufactured systems where by the owner will establish and manage a primary inventory of cold compression therapy systems. Each system includes a unique serial number that will be identified with a particular system throughout the system's useful life. The serial number will be entered into an inventory database upon manufacture of the system. It may be identified on the device via a microchip embedded therewithin or by a simple bar coding label. The serial may be assigned to a particular licensee for distribution, which will allow the device to be tracked anywhere throughout the inventory chain via GPS.

Each licensee will have a unique licensee number issued to it by the system owner. In order for the system to be issued to a particular licensee, the serial number of the system will be coupled to the licensee number to establish a sub-licensee inventory. Thereafter, the cold compression therapy system and method in accordance with the invention is ready for patient use. The licensee may place the system at health care providers, such as hospitals and clinics, at no charge.

The system may communicate directly to an authorizer website by Internet hard line USB style connection, Wi Fi interface, or cellular phone connection inside the device. The system will also include GPS tracking hardware.

The system is capable of electronic remote activation via the Internet for use by the patient. The licensee may communicate remotely with the system to add additional units of time for an existing patient, track the system via GPS for inventory control, or ship the device to a different end user without ever physically taking position of the device. The system will have the ability to collect medical data such as number of times used, duration of time and temperature and have relevant data transferred back to the patient's doctor.

Invoicing and all accounting transactions are automatic upon activation. As an example, assume the patient has agreed to rent the system for two weeks. The serial number of the system is associated with a licensee number on the authorizer website. Payment method will be entered on the authorizer website, for example cash or credit card. After the payment transaction clears, the authorizer website will issue a password that can be remotely uploaded or manually uploaded into the system and which activates the system for the specified number of units of time or, alternatively, the patient may be free to use the system as many times as they choose within the allotted rental time frame.

As hereinbefore disclosed, the system may include built in smart mobile technology such as Wi Fi, Cellular and direct cable connection to the Internet.

Although the present invention has been described with reference to preferred embodiments, workers skilled in the art will recognize that changes may be made in form and detail without departing from the spirit and scope of the invention.

We claim:

1. A thermal therapy system, comprising:
    a joint conforming wrap including a skin contacting surface;
    a first chamber housing one or more inflatable members;
    a second chamber proximate the skin contacting surface; and
    a plurality of wrap thermoelectric modules positioned within the second chamber, the wrap thermoelectric modules each independently configured to cool and heat and form controllable thermoelectric module zones, the wrap thermoelectric modules having
    a front side and
    a back side,
    the front side of the plurality of thermoelectric modules being in direct thermal contact with the skin contacting surface; and
    the one or more inflatable members being disposed to compress the second chamber and thereby press the skin contacting surface against a patient's skin upon inflation of the one or more inflatable members, for provision of thermal therapy from the front side of the wrap thermoelectric modules to the patient's skin through the skin contacting surface;

a power supply module for supplying power to said joint conforming wrap;

a cable operably coupling the wrap and the power supply module;

a fluid circulation pump operably controlled by a controller to pump a thermal fluid through the second chamber to remove heat from the back side of the plurality of thermoelectric modules when the thermoelectric modules provide cooling to the skin;

one or more temperature sensors positioned in the second chamber adapted to provide feedback to the controller; and wherein the power supply module comprises a switching function for controlling the wrap thermoelectric modules in each of the thermoelectric module zones to enable switching between cooling and heating.

2. The thermal therapy system of claim 1 wherein said power supply module further comprises a heat exchanger unit, an electrical power supply, a fluid compression pump and a controller, said controller operable to control said heat exchanger unit, said electrical power supply and said fluid compression pump.

3. The thermal therapy system of claim 2 wherein said heat exchanger unit includes a heat exchanger, one or more heat exchanger thermoelectric modules and the fluid circulation pump for operably circulating the thermal fluid into contact with said one or more heat exchanger thermoelectric modules and said heat exchanger.

4. The thermal therapy system of claim 2 further comprising user control options operably coupled to the electrical power supply, the wrap thermoelectric modules and the controller to control temperature of the wrap and duration of therapy.

5. The thermal therapy system of claim 3 wherein said plurality of thermoelectric modules are operably coupled to said controller, electrical power supply and fluid circulation pump by a plurality of conduits.

6. The thermal therapy system of claim 3 wherein said thermal fluid is selected from water, ethylene glycol, propylene glycol and combinations of the foregoing.

7. The power supply module of claim 3 wherein the fluid circulation pump is in operable arrangement with the controller and adapted to pump a thermal fluid through the wrap thermoelectric modules.

8. The thermal therapy system of claim 3 wherein said fluid compression pump is fluidly coupled to said one or more inflatable members for inflating and deflating the inflatable member to control compression of the skin contacting surface against a patient's skin.

9. The thermal therapy system of claim 1 further comprising a hard case or a soft case removably coupled to or permanently attached to the power supply module.

10. The thermal therapy system of claim 1 wherein said second chamber is encased in a thermally conductive fabric selected from nylon, polyesters or combinations of the foregoing thermally conductive fabrics and a metal selected from aluminum, copper, silver or combinations of the foregoing metals.

11. The thermal therapy system of claim 10 wherein the thermally conductive fabric comprises the skin contacting surface.

12. The thermal therapy system of claim 10 wherein the thermally conductive fabric is in contact with the skin contacting surface.

13. The thermal therapy system of claim 1 wherein said cable is removably coupled to the power supply module.

14. The thermal therapy system of claim 1 wherein said cable is permanently coupled to the power supply module.

15. The thermal therapy system of claim 1 wherein said cable includes an outer surface comprising a thermal conductive material and a lumen therewithin.

16. The thermal therapy system of claim 15 wherein said lumen operably receives a plurality of fluid flow conduits, a fluid compression conduit, an electrical power conduit and a digital conduit.

17. A thermal therapy system of claim 1 wherein the cable comprises a plurality of fluid flow conduits therein for fluidly coupling the first and second chambers of the wrap to the power supply module, and wherein the wrap is configured for flow of the thermal fluid through the wrap thermoelectric modules for removal of the heat.

* * * * *

UNITED STATES PATENT AND TRADEMARK OFFICE
CERTIFICATE OF CORRECTION

| | | |
|---|---|---|
| PATENT NO. | : 11,382,789 B2 | Page 1 of 1 |
| APPLICATION NO. | : 16/230143 | |
| DATED | : July 12, 2022 | |
| INVENTOR(S) | : Lee et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 26 days.

Signed and Sealed this
First Day of August, 2023

Katherine Kelly Vidal
*Director of the United States Patent and Trademark Office*